United States Patent
Pajunk et al.

(10) Patent No.: US 11,167,114 B2
(45) Date of Patent: Nov. 9, 2021

(54) SET FOR PERIPHERAL NERVE BLOCKING

(71) Applicant: Pajunk GmbH Medizintechnologie, Geisingen (DE)

(72) Inventors: Horst Pajunk, Geisingen (DE); Heinrich Pajunk, Geisingen (DE)

(73) Assignee: Pajunk GmbH Medizintechnologie, Geisingen (DE)

( * ) Notice: Subject to any disclaimer, the term of this patent is extended or adjusted under 35 U.S.C. 154(b) by 578 days.

(21) Appl. No.: 14/767,990

(22) PCT Filed: Dec. 20, 2013

(86) PCT No.: PCT/EP2013/077618
§ 371 (c)(1),
(2) Date: Aug. 14, 2015

(87) PCT Pub. No.: WO2014/124719
PCT Pub. Date: Aug. 21, 2014

(65) Prior Publication Data
US 2015/0367103 A1    Dec. 24, 2015

(30) Foreign Application Priority Data
Feb. 15, 2013 (DE) .................. 10 2013 101 538.7

(51) Int. Cl.
*A61M 25/06* (2006.01)
*A61N 1/05* (2006.01)
(Continued)

(52) U.S. Cl.
CPC ..... *A61M 25/0606* (2013.01); *A61B 17/3401* (2013.01); *A61M 25/0043* (2013.01);
(Continued)

(58) Field of Classification Search
CPC .............. A61M 25/00; A61M 25/0606; A61M 25/0043; A61M 2025/002; A61M 25/01;
(Continued)

(56) References Cited

U.S. PATENT DOCUMENTS 3,397,699 A    8/1968    Kohl
4,239,042 A *  12/1980  Asai ........................ A61M 25/01
                                                                128/207.29
(Continued)

FOREIGN PATENT DOCUMENTS

AT    406121    2/2000
DE    19807487  8/1999
(Continued)

OTHER PUBLICATIONS

Patent Cooperation Treaty, "Third Party Observations", issued in International Application No. PCT/EP2013/077618, document of 51 pages, dated Feb. 9, 2015.
(Continued)

*Primary Examiner* — Nilay J Shah
(74) *Attorney, Agent, or Firm* — Akerman LLP; Peter A. Chiabotti

(57) ABSTRACT

A set for peripheral nerve blocking, including a rigid cannula, an outer catheter sleeve which can be slid over the cannula, where the distal tip of the cannula protrudes over the distal end of the catheter sleeve, an inner catheter which can be inserted through the catheter sleeve after removal of the cannula from the catheter sleeve and which has an outlet opening at the distal end, and a first connector piece at the proximal end of the catheter sleeve, where the inner catheter has a second connector piece complementary to the first connector piece, and the inner catheter can be fixed in an axial position by connecting the first connector piece and the second connector piece in the catheter sleeve, in which axial
(Continued)

position the distal end of the inner catheter protrudes from the distal end of the catheter sleeve with a pre-defined length which has the outlet opening.

13 Claims, 3 Drawing Sheets

(51) Int. Cl.
*A61B 17/34* (2006.01)
*A61M 25/00* (2006.01)
*A61M 19/00* (2006.01)

(52) U.S. Cl.
CPC .......... *A61N 1/0551* (2013.01); *A61M 19/00* (2013.01); *A61M 2025/0007* (2013.01); *A61M 2025/0008* (2013.01); *A61M 2025/0059* (2013.01); *A61M 2025/0063* (2013.01)

(58) Field of Classification Search
CPC .......... A61M 19/00; A61M 2025/0007; A61M 2025/0059; A61M 2025/0063; A61M 2025/0183; A61M 25/0015; A61M 25/007; A61B 17/3401; A61B 17/3415
See application file for complete search history.

(56) References Cited

U.S. PATENT DOCUMENTS

| | | | |
|---|---|---|---|
| 4,318,402 A | | 3/1982 | Vaillancourt |
| 4,613,329 A * | | 9/1986 | Bodicky ............ A61M 25/0111 356/139.01 |
| 4,629,450 A * | | 12/1986 | Suzuki .............. A61M 25/0606 604/104 |
| 6,193,686 B1 * | | 2/2001 | Estrada ................. A61M 25/09 604/103.09 |
| 6,228,073 B1 * | | 5/2001 | Noone .............. A61M 25/0014 128/912 |
| 6,231,568 B1 | | 5/2001 | Loeb et al. |
| 6,824,532 B2 | | 11/2004 | Gillis et al. |
| 6,830,561 B2 | | 12/2004 | Jansen et al. |
| 7,682,337 B2 * | | 3/2010 | Valaie ................ A61B 17/3415 604/164.01 |
| 2002/0052576 A1 * | | 5/2002 | Massengale ...... A61M 25/0043 604/164.01 |
| 2003/0051735 A1 * | | 3/2003 | Pavcnik ............. A61B 17/0057 128/831 |
| 2004/0039373 A1 | | 2/2004 | Harding et al. |
| 2005/0049663 A1 | | 3/2005 | Harris et al. |
| 2005/0090801 A1 | | 4/2005 | Racz et al. |
| 2006/0079830 A1 | | 4/2006 | Putz |
| 2006/0129102 A1 | | 7/2006 | Putz |
| 2008/0058757 A1 | | 3/2008 | Pajunk et al. |
| 2008/0154136 A1 | | 6/2008 | Webler |
| 2009/0018511 A1 * | | 1/2009 | Fujii ..................... A61M 5/158 604/195 |
| 2009/0187140 A1 | | 7/2009 | Racz |
| 2009/0198218 A1 | | 8/2009 | Gill et al. |
| 2012/0123391 A1 | | 5/2012 | Gill et al. |

FOREIGN PATENT DOCUMENTS

| | | |
|---|---|---|
| DE | 10215191 | 10/2003 |
| DE | 102006020363 | 10/2007 |
| EP | 0564859 | 10/1993 |
| EP | 1002500 | 5/2000 |
| EP | 1849493 | 10/2007 |
| WO | 2008/082170 | 7/2008 |

OTHER PUBLICATIONS

Patent Cooperation Treaty, "International Search Report" and translation thereof, issued in International Application No. PCT/EP2013/077618, by European Searching Authority, document of 8 pages, dated Mar. 12, 2014.
EPIMED International Inc., "Opposition to German Patent No. 10 2013 101 538," and translation thereof, filed in German Patent No. 10 2013 101 538, document of 37 pages, Apr. 17, 2015.
Wiley Spinal Production Description, www.wileyspinal.com, publication date unknown, filed in German Patent No. 10 2013 101 538 on Apr. 17, 2015, document of 2 pages.
Wiley Spinal Insertion Instructions, www.wileyspinal.com, publication date unknown, filed in German Patent No. 10 2013 101 538 on Apr. 17, 2015, document of 2 pages.
Email dated May 26, 2011 from Mr. Diebold to Dr. Finucane, publication date unknown, filed in German Patent No. 10 2013 101 538 on Apr. 17, 2015, document of 2 pages.
Email dated May 30, 2011 from Dr. Finucane to Mr. Diebold, publication date unknown, filed in German Patent No. 10 2013 101 538 on Apr. 17, 2015, document of 2 pages.
Email dated Mar. 21, 2012 from Mr. Diebold to Dr. Ozelsel, publication date unknown, filed in German Patent No. 10 2013 101 538 on Apr. 17, 2015, document of 2 pages.
Vlessides, "Rapid Reversal of Spinal Anesthesia Follows Cerebrospinal Lavage," Anesthesiology News, Clinical Anesthesiology, Issue Oct. 2009, vol. 35:10, Sep. 21, 2010, document of 2 pages.
Jarrett and Wiley, Poster, Dartmouth-Hitchcock Medical Center, publication date unknown, filed in German Patent No. 10 2013 101 538 on Apr. 17, 2015, document of 2 pages.
Pajunk, "E-Cath according to Tsui, The revolutionary technique for continuous peripheral nerve blocks," Oct. 2014, document of 12 pages.

* cited by examiner

SET FOR PERIPHERAL NERVE BLOCKING

CROSS REFERENCE TO RELATED APPLICATIONS

This application is a § 371 National Phase of PCT/EP2013/077618, filed Dec. 20, 2013, which claims priority to German Patent Application No. 10 2013 101 538.7, filed Feb. 15, 2013.

BACKGROUND

The application relates to a set for peripheral nerve blocking according to the features and structures disclosed herein.

SUMMARY

Peripheral nerve blocking is used for surgical or analgesic treatment of extremities. In this process, a cannula is inserted into the perineural and the catheter is guided through the cannula and inserted into the perineural space as far as the area of the nerve to which the anesthetic is to be administered.

EP 1 002 500 A1 discloses a set for peripheral nerve blocking, comprising a rigid cannula for puncturing the perineural space. The distal cannula tip can be positioned by electrical stimulation in particular. An outer catheter sleeve can be pushed onto the cannula; when performing the puncture, this sleeve is inserted together with the cannula into the patient's body. As soon as the tip of the cannula has reached the destination, the cannula is extracted and an inner catheter is advanced through the remaining catheter sleeve until its distal end protrudes distally out of the catheter sleeve. Then an anesthetic can be injected through the inner catheter. The catheter sleeve has a Luer Lock connector part on its proximal end for connecting a syringe or a tube connector. The axial position of the inner catheter in the catheter sleeve is indicated by markings on the inner catheter. To be able to introduce an anesthetic through the inner catheter, a connection adaptor is attached to the proximal end of the inner catheter.

The present disclosure provides a set for peripheral nerve blocking, which will enable simple handling and reliable positioning.

The present application provides a set for peripheral nerve blocking according to the features and structures disclosed herein.

Advantageous embodiments are disclosed herein.

In addition, the disclosure relates to a method for peripheral nerve blocking having the features and structures disclosed herewith.

The set according to the disclosure has a rigid cannula, which is used for puncturing the peripheral perineural space. The cannula is preferably designed as a unipolar stimulation cannula in an essentially known way; it is made of steel, for example, and is provided with an electrically insulating coating that exposes only the distal tip of the cannula. The precise position of the distal cannula tip is determined by electrostimulation by means of a stimulator connected proximally to the cannula. A catheter sleeve is pushed onto the cannula and is introduced into the perineural space by means of the cannula. The catheter sleeve is manufactured as a flexible nonconductive tubular sleeve made of Teflon, for example, with a small wall thickness. In order for the distal end of the catheter sleeve to be in contact suitably with the distal tip of the cannula, the catheter sleeve sits on the outside circumference of the cannula with a slight radial elastic tension, wherein the distal tip of the cannula remains free for the electrical stimulation. The distal end of the catheter sleeve has a thin wall and tapers conically at the distal end, so that the catheter sleeve together with the cannula can penetrate easily through body tissue.

As soon as the cannula with the catheter sleeve pushed onto it is positioned in the perineural space, the cannula is extracted from the catheter sleeve. Then an inner catheter is inserted through the catheter sleeve. The inner catheter is a soft, flexible length of tubing, which serves to supply a liquid anesthetic. At the proximal end, the inner catheter has a syringe connection for introducing the anesthetic, while there is at least one outlet opening on the distal end.

The inner catheter reinforces the thin-walled flexible catheter sleeve, so that the unit consisting of the catheter sleeve and the inner catheter is non-buckling. Accurate positioning of the distal outlet opening of the inner catheter is possible by means of the catheter sleeve, in that the inner catheter is advanced forward to the distal tip in the catheter sleeve. The inner catheter may also be positioned so that it protrudes out of the distal end of the catheter sleeve by a variable length. The soft flexible distal end of the inner catheter, which protrudes distally out of the catheter sleeve, makes it possible to advance in the perineural space, wherein the soft flexible distal tip of the inner catheter can yield to any resistance in the tissue structure. The risk of damage to the neural tissue in placement of the tip is significantly reduced in this way. The variable axial arrangement of the inner catheter in the catheter sleeve permits adaptation of the length of the free soft flexible tip of the inner catheter to the anatomical conditions during the advance into the perineural space. The set therefore combines the optimal smoothness and thinness of the catheter sleeve over its entire length, for advancing through the skin and the tissue, with the soft flexibility of the distal tip of the inner catheter for preventing damage to the tissue structure.

The inner catheter has a proximal connector part, which can be connected directly to the connector part on the proximal end of the catheter sleeve. Proximally from this connector part, the inner catheter continues in an injection tube having a syringe connection at its proximal end.

The direct connection of the inner catheter to the catheter sleeve means that time is saved and handling is facilitated because it reduces the number of steps for assembling the unit comprising the catheter sleeve and the inner catheter. Furthermore, this makes it possible to prevent an inadvertent wrong connection. Since the inner catheter develops directly into the injection tubing on the connector part, it is possible to inject directly through the syringe connection, without requiring an additional catheter adaptor. When connecting the inner catheter to the catheter sleeve, the injection tubing is connected to the syringe connection without requiring any additional components and without any additional manipulations on the part of the user, in particular for continuous nerve blocking.

In placement of the inner catheter, a liquid can be injected through the injection tubing. The user can observe the fluid spreading in the perineural space by means of ultrasound. The liquid serves to dilate the nerve channel or perineural space to enable a friction-free forward movement of the distal tip of the inner catheter. The liquid may be, for example, an anesthetic or a solution of dextrose in water, for example.

In an advantageous embodiment, the inner catheter not only has at least one distal outlet opening but also has at least one proximal outlet opening in its wall. This at least one proximal outlet opening is arranged axially in the wall of the inner catheter, so that it opens into the annular space between the outside surface of the inner catheter and the inside surface of the catheter sleeve on insertion of the inner catheter into the catheter sleeve. If a liquid is introduced through the inner catheter, this liquid passes not only through the distal outlet openings but also through the proximal outlet opening. The liquid thus fills up the annular space between the inner catheter and the catheter sleeve over the total axial length between the proximal outlet opening of the inner catheter and the distal opening of the catheter sleeve. The liquid filling this annular space results in a definite ultrasonic visibility. The unit consisting of the catheter sleeve and the inner catheter thus becomes definitely visible ultrasonically over its total length, which facilitates positioning and any correction of position. By alternately injecting fluid and aspirating fluid, the ultrasonic reflection of the annular space can be varied, so that ultrasonic detectability is additionally improved.

BRIEF DESCRIPTION OF THE DRAWINGS

The features and structures of the present disclosure are explained in greater detail below on the basis of exemplary embodiments that are illustrated in the drawings, in which.

DETAILED DESCRIPTION OF THE ILLUSTRATED EMBODIMENT

The set for peripheral nerve blocking consists of a cannula 10, catheter sleeve 20 and an inner catheter 30.

Figure 1:
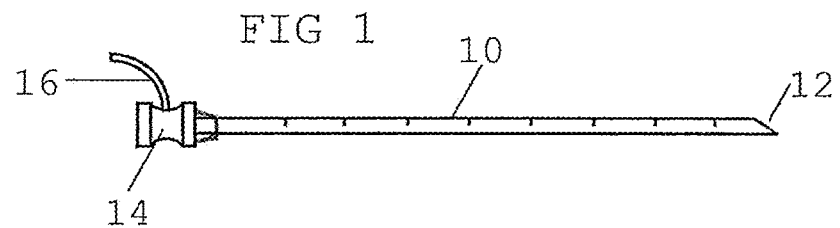
FIG. 1 shows a cannula of the set.

The cannula 10, which is shown as an example in FIG. 1, is preferably designed as a unipolar stimulation cannula. It has a rigid tubular shaft, preferably made of steel, whose distal tip 12 may be designed as a Tuohy tip with a Facet tip or a Sprotte tip in an essentially known way. Over its entire length, the cannula 10 is provided with an outer electrically insulating coating, which exposes only the distal tip 12. An attachment 14 made of plastic, through which a connecting cable 16 is passed, is attached at the proximal end of the cannula 10. The connecting cable 16 contacts the electrically conducting metallic cannula 10 and serves to connect an electric stimulator.

Figure 2:
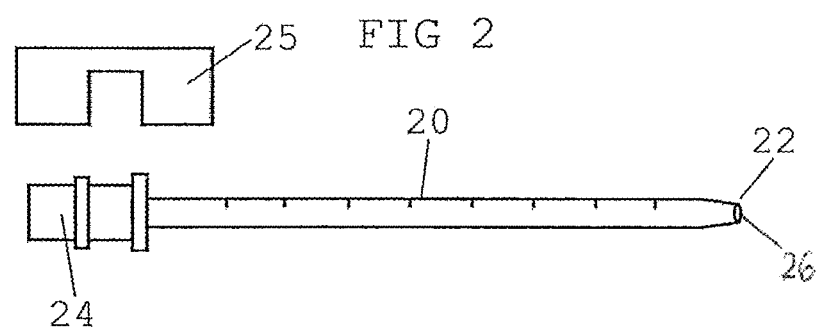
FIG. 2 shows a catheter sleeve of the set.

The catheter sleeve 20, which is shown as an example in FIG. 2, is a flexible catheter made of a soft, non-conducting plastic. The distal end 22 of the catheter sleeve 20 is designed to taper conically toward the distal end. On the distal end 22, the catheter sleeve 20 has a coaxial outlet opening 26. A first connector part 24, which is designed as a female Luer Lock connector part is provided on the proximal end of the catheter sleeve 20. A wing 25 can be attached to the connector part 24, either removably or not removably.

Figure 4:
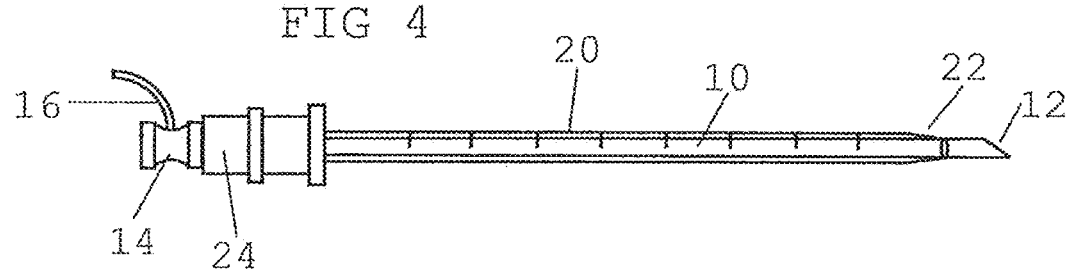
FIG. 4 shows the cannula with the catheter sleeve pushed onto it.

As FIG. 4 shows, the catheter sleeve 20 can be pushed onto the cannula 10, preferably with the help of the wing 25. The length of the cannula 10 and the length of the catheter sleeve 20 are coordinated with one another, so that the distal tip 12 of the cannula 10 protrudes distally out of the distal end 22 of the catheter sleeve 20 when the catheter sleeve 20 has been pushed completely onto the cannula 10 and the proximal attachment 14 of the cannula 10 engages in the connector part 24 of the catheter sleeve 20. The diameter of the distal end 22 of the catheter sleeve 20 is such that the distal end 22 is in contact radially with the outside circumference of the cannula 10 under a slight elastic prestress. The tight contact of the distal end 22 and its conical design produce a continuous transition from the distal tip 12 of the cannula 10 to the distal end 22 of the catheter sleeve 20. Therefore, easy penetration of the cannula 10 with the catheter sleeve 20 pushed onto it through the patient's skin and tissue in puncturing is thereby enabled.

Figure 3:
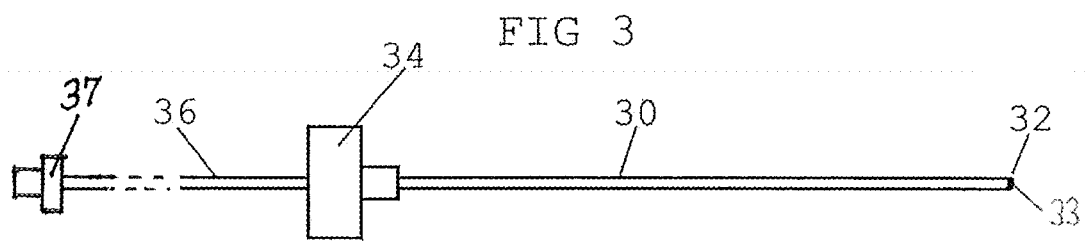
FIG. 3 shows an inner catheter of the set.

The inner catheter 30 shown as an example in FIG. 3 consists of a soft flexible tubing line, whose outside diameter is slightly smaller than the inside diameter of the catheter sleeve 20. On the distal end 32, the inner catheter 30 has at least one outlet opening 33. A single coaxial outlet opening 33 is provided in the exemplary embodiment shown here. Within the scope of the disclosure, radial outlet openings may be provided either additionally or exclusively. A second connector part 34 is arranged on the proximal end of the inner catheter 30. A second connector part 34 is arranged on the proximal end of the inner catheter 30. The second connector part 34 of the inner catheter 30 is designed to be complementary to the first connector part 24 of the catheter sleeve 20, i.e., as a male Luer Lock connector part in the exemplary embodiment illustrated here. The inner catheter 30 is designed as a hollow tube of plastic and may optionally also contain a metal reinforcing wire, a spiral wire or a stimulation wire. The inner catheter 30 is elastically flexible but is still sufficiently stable to resist bending, bulging or kinking. In the connector part 34, the inner catheter 30 develops into an injection tube 36, which is connected proximally and has a syringe connection 37 on its proximal end. A liquid can be supplied to the inner catheter 30 through the syringe connection 37 by means of a syringe (not shown).

Figure 5:
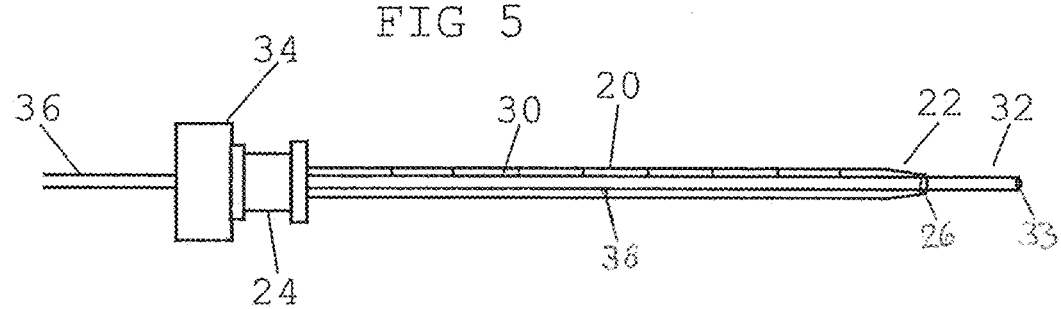
FIG. 5 shows the catheter sleeve with the inner catheter inserted.

As FIG. 5 shows, the length of the catheter sleeve 20 and the length of the inner catheter 30 are coordinated with one another, so that the distal end 32 of the inner catheter 30 protrudes distally out of the distal end 22 of the catheter sleeve 20 when the inner catheter 20 is inserted completely into the catheter sleeve 20, so that the second connector part 34 of the inner catheter 30 engages with the first connector part 24 of the catheter sleeve 20, and the two connector parts 24 and 34 are joined together. Since the inside diameter of the catheter sleeve 20 is slightly larger than the outside diameter of the inner catheter 30, there remains an annular space 38 between the outside diameter of the inner catheter 30 and the inside diameter of the catheter sleeve 20.

The method for peripheral nerve blocking with the set illustrated here is carried out as follows:

First, the catheter sleeve 20 is pushed onto the cannula 10 until the connector part 24 is engaged with the attachment 14 on the cannula 10. The distal tip 12 of the cannula 10 protrudes out of the distal end 22 of the catheter sleeve 20, as shown in FIG. 4. The cannula 10 is connected to an electric nerve stimulator by means of the connecting cable 16. Then the cannula 10 is pushed through the patient's skin and tissue into the perineural space, wherein the positioning of the tip 12 of the cannula is monitored by means of electric nerve stimulation. Since the distal end 22 of the catheter sleeve 20 is designed to be conical and is in contact with the cannula 10 under elastic prestress, the catheter sleeve 20 can be inserted together with the cannula 10 without any additional resistance.

As soon as the tip 12 of the cannula 10 has been positioned in the perineural space, the catheter sleeve 20 can be advanced in the distal direction on the cannula 10 as needed, so that the distal end 22 of the catheter sleeve 20 is advanced further into the perineural space beyond the tip 12 of the cannula 10. As soon as the catheter sleeve 20 is positioned with such a distal advance or even without such a distal advance, the cannula 10 is extracted out of the catheter sleeve 20. After the cannula 10 has been extracted out of the catheter sleeve 20, the inner catheter 30 is inserted into the catheter sleeve 20 from the proximal end. First, the inner catheter 30 is inserted into the catheter sleeve 20 until its distal end 32 comes out of the distal end 22 of the catheter sleeve 20. In this advance of the inner catheter 30, a liquid can be supplied to the inner catheter 30 via the injection tube 36, emerging at the distal outlet opening 33 catheter. This liquid may serve to widen the space through which the inner catheter 30 is advanced, optionally together with the catheter sleeve 20. The liquid thus forms a cushion, which facilitates the forward movement of the distal end 32. An aqueous dextrose solution, for example, may serve as the liquid.

With the combined advance of the catheter sleeve 20 and the inner catheter 30, the inner catheter 30 serves to reinforce the soft flexible catheter sleeve 20 over its entire length, so that kinking and bending of the catheter unit, consisting of the catheter sleeve 20 and the inner catheter 30, are prevented. The length of the distal end 32 protruding distally out of the catheter sleeve 20 may be varied, so that the catheter unit has a distal tip formed by the protruding distal end 32 of the inner catheter 30, this distal tip having a softer flexibility and being able to yield to tissue structures without damaging them. The length of the protruding distal end 32 may be adapted to the respective anatomical conditions of its use.

The liquid emerging from the distal outlet opening 33 of the inner catheter 30 allows the position of the distal end 32 of the inner catheter and thus the catheter unit consisting of the inner catheter 30 and the catheter sleeve 20 to be observed by means of ultrasound.

As soon as the distal end 32 of the inner catheter 30 is optimally positioned in the perineural space, the catheter sleeve 20 is retracted proximally until the first connector part 24 of the catheter sleeve 20 engages with the second connector part 34 of the inner catheter 30, whereupon the two connector parts 24 and 34 are connected. The catheter unit, consisting of the connector sleeve 20 and the inner catheter 30 connected to it, can then remain in its position for continuous anesthesia or for a possible subsequent redosing. An anesthetic is supplied through the syringe connection 37 and the injector tube 36.

Figure 6:
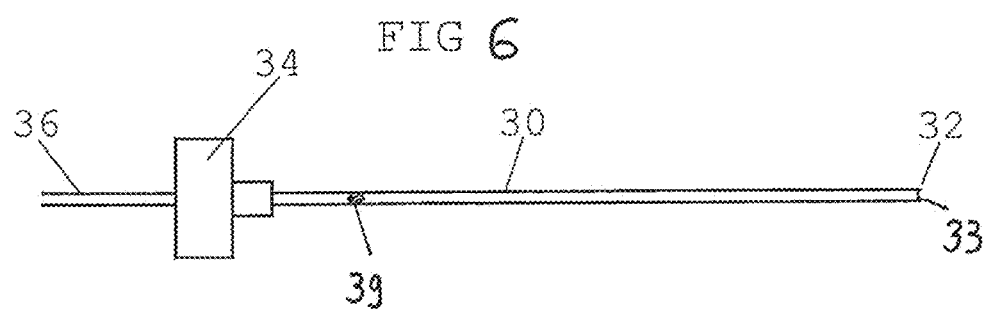
FIG. 6 shows the inner catheter in a second embodiment.
Figure 7:
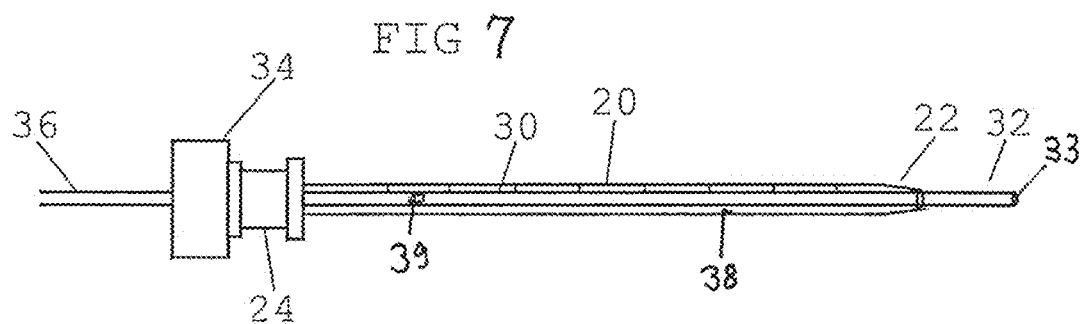
FIG. 7 shows the catheter sleeve with the inner catheter inserted in the second embodiment.

FIGS. 6 and 7 show a modified second embodiment of the inner catheter 30. In this embodiment, the inner catheter 30 corresponds to the embodiment of FIG. 3 described above and differs only in that at least one proximal outlet opening 39 is provided in the wall of the inner catheter 30 in addition to the at least one outlet opening 33 on the distal end. The proximal outlet opening 39 is arranged in an axial position near the second connector part 34, such that this proximal outlet opening 39 opens into the annular space 38 between the inner catheter 30 and the catheter sleeve 20 when the inner catheter 30 is inserted into the catheter sleeve 20. Instead of a proximal outlet opening 39, a plurality of proximal outlet openings may also be provided.

If the inner catheter 30 has been inserted into the catheter sleeve 20, as shown in FIG. 7, a liquid can be supplied through the injection tubing 36. This liquid emerges through the distal outlet opening 33, as described in the first exemplary embodiment. Furthermore, the liquid comes out through the proximal outlet opening 39 and flows into the annular space 38 in the distal direction, where it emerges through the outlet opening 26 on the distal end 22 of the catheter sleeve. The liquid emerging at the distal outlet opening 33 allows ultrasonic observation of the distal end 32 of the inner catheter 30. The liquid in the annular space 38 permits an improved ultrasonic visibility over the entire length of the annular space 38, i.e., over the entire length of the catheter sleeve 20. This yields the advantage that not only can the position of the distal end 32 of the inner catheter 30, improved by means of ultrasound, be observed, but also the position of the catheter unit consisting of the catheter sleeve 20 and the inner catheter 30 is visible ultrasonically in an improved manner over its entire length. Ultrasonic observation of the catheter unit over its entire length may also be improved in addition by the fact that the liquid is alternately injected and aspirated through the injection tubing 36. Therefore, this creates a pulsating axial movement of the liquid in the annular space 38, which results in a varying ultrasonic reflection and thereby makes the catheter unit more clearly recognizable.

LIST OF REFERENCE NUMERALS 10 cannula
12 distal tip
14 attachment
16 connecting cable
20 catheter sleeve
22 distal end
24 first connector part
25 wing
26 outlet opening
30 inner catheter
32 distal and
33 outlet opening
34 second connector part
36 injection tubing
37 syringe connection
38 annular space
39 outlet opening

The invention claimed is:

1. A set for peripheral nerve blocking, comprising:
a rigid cannula for puncturing a perineural space, the rigid cannula having a rigid cannula distal tip;
an outer catheter sleeve with an outer catheter sleeve distal end and an outer catheter sleeve proximal end, wherein the outer catheter sleeve can be pushed onto the rigid cannula such that the rigid cannula distal tip protrudes beyond the outer catheter sleeve distal end;
an inner catheter that can be inserted through the outer catheter sleeve after extraction of the rigid cannula from the outer catheter sleeve, the inner catheter having an inner catheter distal end and an outlet opening on the inner catheter distal end; and
a first connector part on the outer catheter sleeve proximal end,
wherein the inner catheter has a second connector part, which is complementary to the first connector part, and the inner catheter can be secured in the outer catheter sleeve by connecting the first connector part and the second connector part in an axial position, in which the inner catheter distal end protrudes out of the outer catheter sleeve distal end with a predetermined length having the outlet opening;

wherein the inner catheter also has, in addition to the outlet opening on the inner catheter distal end, a proximal outlet opening in a wall of the inner catheter that opens into an annular space between an outside surface of the inner catheter and an inside surface of the outer catheter sleeve when the inner catheter is inserted into the outer catheter sleeve, to allow liquid into the annular space to visualize ultrasonically catheter length thereby facilitating positioning and any correction of position; and wherein the proximal outlet opening is closer to the second connector part than to the outlet opening on the inner catheter distal end.

2. The set according to claim 1, wherein an injection tubing is connected proximally to the inner catheter in the second connector part.

3. The set according to claim 1, wherein the outer catheter sleeve consists of a soft flexible plastic.

4. The set according to claim 3, wherein the outer catheter sleeve tapers conically distally on the outer catheter sleeve distal end.

5. The set according to claim 3, wherein the outer catheter sleeve is in contact with an outside circumference of the rigid cannula with the outer catheter sleeve distal end under elastic prestress.

6. The set according to claim 3, wherein the inserted inner catheter reinforces the outer catheter sleeve against kinking.

7. The set according to claim 1, wherein the first connector part is a female Luer Lock connector part and the second connector part is a male Luer Lock connector part.

8. The set according to claim 1, wherein the outer catheter sleeve has a wing on the outer catheter sleeve proximal end.

9. The set according to claim 1, wherein the inner catheter is made of a flexible plastic.

10. The set according to claim 1, wherein the proximal outlet opening is located at a proximal end of the inner catheter.

11. A method for peripheral nerve blocking comprising:
providing:
a rigid cannula for puncturing a perineural space, the rigid cannula having a rigid cannula distal tip;
an outer catheter sleeve with an outer catheter sleeve distal end and an outer catheter sleeve proximal end, wherein the outer catheter sleeve can be pushed onto the rigid cannula such that the rigid cannula distal tip protrudes beyond the outer catheter sleeve distal end;
an inner catheter that can be inserted through the outer catheter sleeve after extraction of the rigid cannula from the outer catheter sleeve, the inner catheter having an inner catheter distal end and an outlet opening on the inner catheter distal end; and
a first connector part on the outer catheter sleeve proximal end,
wherein the inner catheter has a second connector part, which is complementary to the first connector part, and the inner catheter can be secured in the outer catheter sleeve by connecting the first connector part and the second connector part in an axial position, in which the inner catheter distal end protrudes out of the outer catheter sleeve distal end with a predetermined length having an outlet opening,
wherein the inner catheter also has, in addition to the outlet opening, a proximal outlet opening in a wall of the inner catheter that opens into an annular space between an outside surface of the inner catheter and an inside surface of the outer catheter sleeve when the inner catheter is inserted into the outer catheter sleeve, to allow liquid into the annular space to visualize ultrasonically a total catheter length thereby facilitating positioning and any correction of position of the rigid cannula distal tip;
sliding the outer catheter sleeve onto the rigid cannula;
inserting the rigid cannula together with the outer catheter sleeve slid thereon into a patient's body;
positioning the rigid cannula distal tip in the perineural space;
extracting the rigid cannula out of the outer catheter sleeve while the outer catheter sleeve remains in position;
inserting the inner catheter into the outer catheter sleeve;
positioning the inner catheter distal end;
proximally retracting the outer catheter sleeve along the inner catheter,
connecting the outer catheter sleeve and the inner catheter by the first connector part arranged on the outer catheter sleeve and the second connector part arranged on the inner catheter, and
supplying an anesthetic through the inner catheter by an injector tubing connected proximally to the inner catheter.

12. The method according to claim 11, in which the positioning of the inner catheter distal end is monitored by ultrasonic observation of the liquid which is supplied via the inner catheter and emerges at the inner catheter distal end.

13. The method according to claim 11, in which a position of the outer catheter sleeve and a position of the inserted inner catheter is determined by ultrasonic observation by the liquid introduced into the annular space between the outer catheter sleeve and the inner catheter.

* * * * *